United States Patent [19]

Grandgeorge et al.

[11] Patent Number: 5,371,195
[45] Date of Patent: Dec. 6, 1994

[54] METHOD FOR PURIFYING FACTOR VIII AND PREPARATIONS OBTAINED

[75] Inventors: Michel Grandgeorge, Vaugneray; Charles Lutsch, Grezieu la Varenne, both of France

[73] Assignee: Pasteur Merieux, France

[21] Appl. No.: 948,395

[22] Filed: Sep. 23, 1992

[30] Foreign Application Priority Data

Sep. 26, 1991 [FR] France ................. 91 11849

[51] Int. Cl.$^5$ .............. A61K 35/16; C07G 7/00; C07K 13/00; C07K 31/20
[52] U.S. Cl. .................. 530/383; 530/381; 530/416; 530/417; 530/413; 530/384; 530/420; 530/427
[58] Field of Search .............. 530/38.3, 381, 416, 530/417, 413, 384, 420, 427; 514/12, 21

[56] References Cited

U.S. PATENT DOCUMENTS

| | | | |
|---|---|---|---|
| 4,495,175 | 1/1985 | Chavin et al. | 530/385 |
| 4,508,709 | 4/1985 | Amphlett et al. | 530/383 |
| 4,743,680 | 5/1988 | Mathews et al. | |
| 4,758,657 | 7/1988 | Farb et al. | |
| 5,043,428 | 8/1991 | Heimburger et al. | |
| 5,110,907 | 5/1992 | Kosow et al. | 530/381 |

FOREIGN PATENT DOCUMENTS 323275 11/1989 European Pat. Off. .
367840 5/1990 European Pat. Off. .
WO89/12065 12/1989 WIPO .

OTHER PUBLICATIONS

Vehar et al; "Preparation and Properties of Bovine ... "; Biochem, vol. 19, No. 3, Feb. 5, 1980, pp. 401–410.
Faure et al; "Improved Buffer for the Chromatographic ... "; Journ of Chromatography, vol. 257, 1981, pp. 387–391.
Lundblad et al; "the Effect of Dextrose on Chromatography ... "; Thrombosis Research, vol. 1, 1972, pp. 197–200.

Primary Examiner—Howard E. Schain
Assistant Examiner—Lynn Touzeau
Attorney, Agent, or Firm—Larson and Taylor

[57] ABSTRACT

In the method for purifying factor VIII from cryoprecipitate, which is dissolved and then treated with alumina gel, the extract is diluted to a protein concentration not exceeding approximately 5 g/l and subjected to viral inactivation with solvent/detergent, the inactivated extract containing the solvent/detergent is then subjected to chromatography on a weak anion exchange column which is hydrophilic in nature and factor VIII is then eluted with a dissociating buffer.

8 Claims, No Drawings

METHOD FOR PURIFYING FACTOR VIII AND PREPARATIONS OBTAINED

BACKGROUND OF THE INVENTION

1. Field of the Invention

The present invention relates to a new method for purifying factor VIII from cryoprecipitate of human or animal blood, as well as to the preparations obtained by this method.

2. Description of Related Art

The importance of attempting to obtain, in good yields, the purest possible fractions, in order to avoid the presence of contaminants such as other blood proteins or foreign products such as antigens, viruses and the like, is known.

Lundblad et al. (Thrombosis Research, 1, p. 197–200, 1972) purify bovine factor VIII by ion exchange chromatography on a column of TEAE-cellulose in 50 mM Tris buffer, pH 8.6, and an NaCl gradient. They obtain a yield of 15 to 45% and a specific activity multiplied by 25 to 50. The addition of 50 mM glucose to the buffer increases the yield to 60–70% for a specific activity substantially identical to the above.

Vehar and Davie (Biochemistry, 19 (3), p. 401–410, 1980) purify bovine factor VIII on DEAE-Sephadex in 20 mM imidazole buffer, pH 6.6, also containing: 0.15 M NaCl, 10 mM $CaCl_2$, 20 mM glycine ethyl ester, 10% glycerol, and dithiothreitol. The yield is 75% and the specific activity is multiplied by 103.

Faure et al. (Journal of Chromatography 257, p. 387–391, 1983) purify human factor VIII on an anion exchanger having hydrophobic properties due to hexyl residues (AH-SEPHAROSE). The solution to be purified is a cryoprecipitate extract treated with alumina gel. Using a 0.1 M/0.1 M acetate/lysine equilibration buffer, pH 5.5, the yield is 34% for a specific activity multiplied by 7.7. The addition of sucrose (10 g/l) and albumin (10 g/l) to this buffer is said to increase the yield.

In European Patent Application EP-A-0,173,242, a method is described for purifying factor VIII, in which a cryoprecipitate extract treated with alumina gel undergoes chromatography on an anion exchanger of the polysaccharide type at an acid pH of between 5 and 6.5 and preferably 5.5. This method is noteworthy in that, prior to the chromatography, the cryoprecipitate extract is pasteurised and in that this chromatography is performed in the presence of sucrose and glycine at high concentrations.

U.S. Pat. No. 4,743,680 recommends, on the one hand the use of sugars and polyhydric alcohols to increase the electrostatic forces at the surface of the factor VIII protein and decrease the hydrophobicity during chromatography on an ion exchange column, and on the other hand the use of a surfactant such as Tween 80 in the chromatographic elution buffer. Suggested supports are QAE-SEPHADEX A-25 and QAE-SEPHAROSE 4B-Fast Flow (Pharmaci, Sweden).

U.S. Pat. No. 4,758,657 proposes the purificatication of factor VIII on a hydrophobic support which is not an anion exchanger, and the use of an elution buffer comprising surfactants.

From European Patent Application EP-A-0,343,27, a method is also known for purifying factor VIII, in which, principally, a cryoprecipitate extract is treated with alumina gel at a temperature of between 10° and 18° C. and is subjected to chromatography on a hydrophilic anion exchange column (for example on DEAE-FRACTOGEL). The method comprises a viral inactivation step, using a solvent/detergent system (for example TWEEN/TNBP) which can then be removed before the chromatography step by oil extraction. In addition, this document explains that it is essential to perform the extraction of the cryoprecipitate in a medium containing heparin. A similar treatment is described in Patent Application EP-A-0,367,840.

International Patent Application WO 89/12,065 describes a method which is based substantially on the above (EP-A-0,343,275). This document lays stress, however, on the choice of the chromatography resin so as to permit separation on a single chromatography column and avoid subsequent treatments, such as ultrafiltration, which, according to this application, increase the complexity of the methods and decrease the activity of the protein. The choice of resin settles on a gel of vinyl polymer containing DEAE groups, with slightly hydrophobic properties and having a special capacity to adsorb the very large factor VIII/von Willebrand factor complexes. FRACTOGEL TSK-DEAE 650 (M) (Merck) complies with this definition and hence proves markedly superior to other types of gels such as DEAE-SEPHAROSE CL-6B, DEAE-SEPHAROSE CL-6B Fast Flow (Pharmacia), DEAE-SEPHAROSE 4B and DEAE-Trisacryl LS (IBF), which are not recommended.

This document also recommends the use of glycine and lysine in the elution buffer and avoids the use of calcium chloride in this buffer. In addition, inactivation with solvent/detergent is optional and may be carried out at any stage of the method. The chromatographic yield is between 75 and 90% and the specific activity of the factor VIII is greater than 100 IU/mg.

SUMMARY OF THE INVENTION

The objective of the present invention is to provide a new method for purifying factor VIII from cryoprecipitate, enabling chromatographic yields of more than 90% to be achieved.

The method according to the invention eliminates various drawbacks of the prior art, and in particular the risks of denaturation by pasteurisation, the use of high sugar concentrations, the presence of Tween 80 in the eluted product or the use of buffers containing glycine and lysine.

The subject of the invention is hence a method for purifying factor VIII from cryoprecipitate, which is dissolved and then treated with alumina gel in the customary manner, the extract then being diluted to a protein concentration not exceeding approximately 5 g/l, in particular 4 g/l, and subjected to viral inactivation with solvent/detergent, the inactivated extract containing the solvent/detergent is then subjected to chromatography on a weak anion exchange column which is hydrophilic in nature, the factor VIII then being eluted with a dissociating buffer, and thereafter optionally subjected to ultra-filtration, to sterilising filtration and/or to lyophilisation.

This method enables the chromatographic yield to improve upon the best known methods, while assuring a factor VIII of at least as good quality. Advantageously, the method according to the invention makes it possible to dispense with the sugars, polyhydric alcohols and amino acids (in particular lysine and glycine) used hitherto in the chromatography steps.

DESCRIPTION OF THE PREFERRED EMBODIMENTS

The essential features of this method which make these improvements possible are, on the one hand the limitation of the protein level during the chromatography step, and on the other hand the presence of the solvent/detergent during binding of the factor VIII to the column, associated with the hydrophilic nature of the latter.

The solvent/detergent system is preferably chosen from the following systems:

TWEEN 80/tri-n-butyl phosphate (TNBP), in particular 1% TWEEN 80/0.3% TNBP, sodium cholate/TNBP, in particular 0.2% sodium cholate/0.3% TNBP.

The chromatography support is preferably polysaccharide in nature, but another weak anion exchanger support which is hydrophilic in nature and capable of separating proteins may be suitable (for example polyacrylamide/polyvinyl support).

An especially preferred support is DEAE-SEPHAROSE Fast Flow. Another suitable support is DEAE-SPERODEX LS (dextran/silica base).

The chromatography buffers can advantageously be the following:

equilibration buffer: 20 mM TRIS-HCl, mM NaCl, pH 6.8;

washing buffer: 20 mM TRIS-HCl, 200 to 210 mM NaCl, pH 6.8; and elution buffer: 200 mM Na acetate, 250 mM $CaCl_2$, pH 6.0.

A further subject of the invention is the factor VIII preparations obtained, which are characterised by a high purity (specific activity, before addition, for example, of human albumin as a stabiliser, of at least approximately 100 IU VIII:C/mg of protein).

The invention will now be described in greater detail by means of non-limiting examples of implementation and comparative examples.

EXAMPLE 1.

5 kg of cryoprecipitate were suspended in 20 l of demineralised water containing approximately 3 IU/ml of heparin. 680 ml of 2% alumina gel were added.

After incubation at neutral pH and a temperature of +4° C., the mixture was centrifuged and the supernatant recovered.

A solution containing 170,100 IU of factor VIII with a specific activity of 1.3 IU VIII:C/mg of protein was obtained.

This solution was diluted to 4 g/l of protein and equilibrated to 20 mM citrate, 100 mM glycine, 60 mM NaCl, 2.5 mM $CaCl_2$, pH 6.8.

Viral inactivation was then performed by incubation for 15 h at 24° C. in the presence of the solvent/detergent mixture: 0.3% TNBP +1% TWEEN 80.

After this operation, the solution which contained 141,100 IU of factor VIII was filtered at room temperature through a 2.5-l column of DEAE-SEPHAROSE Fast Flow gel, pre-equilibrated with 20 mM TRIS-HCl, 150 mM NaCl buffer, pH 6.8.

After washing of the column with 20 mM TRIS-HCl, 210 mM NaCl buffer, pH 6.8, the factor VIII was eluted with 200 mM sodium acetate, 250 mM $CaCl_2$ buffer, pH 6.8.

A solution containing 135,600 IU of purified factor VIII with a specific activity of 141.2 IU VIII:C/mg of protein was obtained, equivalent to a 96.1% chromatographic yield.

At this stage, the excess $CaCl_2$ was removed from the factor VIII, which was equilibrated in a stabilising solution, compatible with intravenous use, by diafiltration and then lyophilised.

The stabilising solution used in this example contained human albumin, so that the final specific activity was lowered to 6.6 IU VIII:C/mg of protein.

EXAMPLE 2.

Influence of Protein Concentration on the Percentage Binding to the Column

The experiments below were carried out on a 145-ml column of DEAE-SEPHAROSE Fast Flow gel. The factor VIII solutions purified with alumina gel were prepared as in Example 1, except for the adjustment of protein level, which was variable.

The solvent/detergent mixture used for viral inactivation was either 0.3% TNBP +1% TWEEN 80, or 0.3% TNBP +0.2% sodium cholate. Injection onto the column, equilibrated as in Example 1, was performed at room temperature at a flow rate of 1 l/h.

The percentage binding of factor VIII to the column was calculated from the VIII:C units not retained on the column (units reappearing in the filtrate).

The results recorded in Table 1 show that the percentage binding of factor VIII to the column is lowered with a protein concentration >5 g/l. At a protein concentration <5 g/l, the percentage binding is always >95% for a quantity of factor VIII of between 3,700 IU VIII:C and 11,200 IU VIII:C.

TABLE 1

| Experiment No. | Solvent/ detergent | Protein concentration g/l | VIII:C units injected | % binding |
|---|---|---|---|---|
| 622-44 | TNBP/TWEEN | 11.2 | 5,467 | 82.3 |
| 622-43 | TNBP/TWEEN | 4.7 | 11,200 | 96.3 |
| 622-45 | TNBP/TWEEN | 4.6 | 4,952 | 95.3 |
| 622-58 | TNBP/TWEEN | 3.1 | 3,773 | 98.5 |
| 622-50 | TNBP/cholate | 7.3 | 7,665 | 82.2 |
| 622-51 | TNBP/cholate | 6.0 | 7,592 | 90.8 |
| 622-47 | TNBP/cholate | 3.9 | 6,351 | 95.7 |
| 622-41 | TNBP/cholate | 3.7 | 6,716 | 96.3 |

EXAMPLE 3.

Comparison of the Chromatography supports DEAE-SEPHAROSE Fast Flow (Pharmacia) and DEAE-SPHERODEX LS (IBF)

These experiments were carried out on a 20 ml column of gel. A single factor VIII solution purified with alumina gel was prepared according to a method similar to that described in Example 1, and then subjected to a viral inactivation treatment with the solvent/detergent mixture 0.3% TNBP +1% Tween 80. The factor VIII had a specific activity at this stage of 1.0 IU VIII:C/mg of protein.

Chromatography was performed under conditions similar to those of Example 1, comparing a DEAE-SEPHAROSE and a DEAE-SPHERODEX support. The chromatographic yield was calculated from the factor VIII units reappearing in the eluate.

The results recorded in Table 2 show that the performance of the two chromatography supports was identical.

TABLE 2

| Experiment No. | Chromatography support | VIII:C units injected | Chromatographic yield | Factor VIII specific activity in the eluate (IU VIII:C/ mg protein) |
| --- | --- | --- | --- | --- |
| 622-18 | DEAE-SPHERODEX | 116 | 92.1% | 113 |
| 622-21 | DEAE-SEPHAROSE | 110 | 93.0% | 115 |

EXAMPLE 4.

Effect of the Absence of the Solvent/Detergent Reagent in the Factor VIII on the Chromatographic Purification This experiment was carried out on a 20-ml column of DEAE-SEPHAROSE Fast Flow gel using factor VIII solution purified with alumina gel according to a method similar to that described in Example 1. The factor VIII had a specific activity at this stage of 1.0 IU VIII:C/mg of protein.

The product was chromatographed directly, without performing a prior solvent/detergent treatment, under identical conditions to experiment 622-21 of Example 3.

The results recorded in Table 3 are less satisfactory than those obtained in Experiment 622-21, in spite of a more favourable protein level at the point of injection (4.5 g/l, against 6.0 g/l in experiment 622-21).

TABLE 3

| Experiment No. | Solvent/ detergent treatment | VIII:C units injected | Chromatographic yield | Factor VIII specific activity in the eluate (IU VIII:C/ mg protein) |
| --- | --- | --- | --- | --- |
| 622-24 | NO | 93 | 80% | 70 |

We claim:

1. Method for purifying Factor VIII from cryoprecipitate containing same, comprising:
   i) dissolving said cryoprecipitate;
   ii) adding alumina gel to the solution of dissolved cryoprecipitate to purify said cryoprecipitate;
   iii) separating purified cryoprecipitate extract from said alumina gel-treated solution of cryoprecipitate;
   iv) diluting said extract to a protein concentration not exceeding approximately 5 g/l and subjecting said extract to viral inactivation with solvent/detergent;
   v) subjecting the inactivated extract containing the solvent/detergent to chromatography with a weak anion exchange column which is hydrophilic in nature; and,
   vi) eluting factor VIII from said column with a dissociating buffer.

2. Method according to claim 1, wherein the eluted factor VIII is subjected to ultra-filtration, sterilizing filtration and lyophilization.

3. Method according to claim 1 wherein a solvent/detergent system is selected from the group consisting of: TWEEN 80/TNBP, and sodium cholate/TNBP.

4. Method according to claim 1, characterized in that said weak anion exchange column is a polysaccharide chromatography support.

5. Method according to claim 4 wherein said polysaccharide chromatography support is DEAE-SEPHAROSE Fast Flow or DEAE-SPHERODEX LS.

6. Method according to one of claims 1, 3 or 5 wherein the buffers used for said chromatography are chosen from at least one of the following buffers:
   equilibration buffer: 20 mM TRIS-HCL, 150 mM NaCL, pH 6.8;
   washing buffer: 20 mM TRIS-HCL, 200 to 210 mM NaCl, pH 6.8; and
   elution buffer: 200 mM Na acetate, 250 mM $CaCl_2$, pH 6.0.

7. A method according to claim 3 wherein the solvent/detergent system is selected from the following group consisting of:
   1% TWEEN 80/0.3% TNBP and
   0.2% sodium cholate/0.3% TNBP.

8. A method according to claim 1 wherein said extract is diluted to a protein concentration of 4 g/l.

UNITED STATES PATENT AND TRADEMARK OFFICE
CERTIFICATE OF CORRECTION

PATENT NO. : 5,371,195

DATED : Dec. 6, 1994

INVENTOR(S) : GRANDGEORGE, et al.

It is certified that error appears in the above-identified patent and that said Letters Patent is hereby corrected as shown below:

On the Title page, item [73];

please change "Pasteur Merieux, France" to

-- PASTEUR MERIEUX Serums et Vaccins, France --.

Signed and Sealed this

Tenth Day of October, 1995

*Attest:*

BRUCE LEHMAN

*Attesting Officer*  *Commissioner of Patents and Trademarks*